United States Patent [19]

Cantrell et al.

[11] Patent Number: 4,803,070

[45] Date of Patent: Feb. 7, 1989

[54] IMMUNOLOGICAL EMULSION ADJUVANTS FOR POLYSACCHARIDE VACCINES

[75] Inventors: John L. Cantrell, Corvallis; Jon A. Rudbach, Hamilton, both of Mont.

[73] Assignee: Ribi ImmunoChem Research Inc., Hamilton, Mont.

[21] Appl. No.: 852,118

[22] Filed: Apr. 15, 1986

[51] Int. Cl.$^4$ .............................................. A61K 39/00
[52] U.S. Cl. ........................................ 424/92; 424/88; 424/89; 514/21; 514/885; 514/937
[58] Field of Search ................... 424/88, 92; 514/885, 514/937, 938, 939, 943

[56] References Cited

U.S. PATENT DOCUMENTS

| | | | |
|---|---|---|---|
| 3,993,775 | 11/1976 | Williams | 514/885 |
| 4,036,953 | 7/1977 | Adam et al. | 514/2 X |
| 4,185,090 | 1/1980 | McIntire | 514/885 X |
| 4,307,229 | 12/1981 | Liav et al. | 514/924 X |
| 4,338,334 | 7/1982 | Jensen | 514/825 X |
| 4,367,727 | 3/1984 | Ribi et al. | 424/177 |
| 4,505,900 | 3/1985 | Ribi et al. | 424/177 |
| 4,606,918 | 8/1986 | Allison | 514/8 X |

OTHER PUBLICATIONS

Davis, et al., Microbiology, Second Edition, 1973, pp. 464–467.
Manning et al., Antibody Response to *Escherichia coli* Lipopolysaccharide and Type III Pneumococcal Polysaccharide by Congenitally Thymusless (Nude) Mice—Journal of Immunology—108, 1470 (1972).
Von Eschen and Rudbach,—Antibody Responses of Mice to Alkaline Detoxified Lipopolysaccharide—Journal of Immunology, 116, (1976).
Von Eschen and Rudbach—Immunological Responses of Mices to Native Protoplasmic Polysaccharide and Lipopolysaccharide—Journal of Experimental Medicine, 140, 1604 (1974).
Milner et al.,—Cellular Responses to Bacterial LipopolySaccharide: T Cells Recognize LPS Determinants—Journal of Immunology, 18, 21 (1983).
J. Munoz—Effect of Bacteria and Bacterial Products on Antibody Response—Advances in Immunology.
Hamaoka and Katz—Cellular Site of Action of Various Adjuvants in Antibody Responses to Hapten-Carrier Conjugates—Journal of Immunology, 111, 1554 (1973).

*Primary Examiner*—Matthew A. Thexton
*Assistant Examiner*—Catherine S. Kilby
*Attorney, Agent, or Firm*—Burgess, Ryan & Wayne

[57] ABSTRACT

An immunological adjuvant for polysaccharide vaccines is provided whereby polysaccharide antigens are rendered more immunogenic and thus stimulate more antibody production including an IgG response and immunological memory. The adjuvant is comprised of (1) either (A) an emulsion system containing a metabolizable oil, a low molecular weight polyol and lecithin, or (B) an oil-in-water emulsion system containing a light hydrocarbon non-biodegradable oil or a biodegradable oil, and a detergent; and (2) a refined detoxified endotoxin. The adjuvant can optionally also contain trehalose dimycolate.

16 Claims, No Drawings

IMMUNOLOGICAL EMULSION ADJUVANTS FOR POLYSACCHARIDE VACCINES

FIELD OF THE INVENTION

This invention relates in general to novel immunological adjuvants for polysaccharide vaccines. In another aspect, this invention relates to novel immunological systems comprised of polysaccharide antigens in combination with certain biological adjuvants in lipid emulsion systems or on oil droplets. In a further aspect, the invention is directed to a method whereby polysaccharide antigens are rendered more immunogenic when combined with the adjuvants of the present invention.

BACKGROUND OF THE INVENTION

Prior to the present invention, it has been reported in the literature that polysaccharide antigens stimulated primarily IgM antibody with little or no IgG response. Moreover, an amnastic response or immunological memory has been difficult to obtain with polysaccharide antigens in experimental animals and in humans. Accordingly, the immunity induced by the use of polysaccharide antigens was short lived. Additionally, polysaccharide vaccines have not proven to be very immunogenic in young children. Therefore, a need existed for a method whereby polysaccharide antigens could be rendered more immunogenic and thus stimulate more antibody production, including an IgG response and immunological memory.

SUMMARY OF THE INVENTION

In its broad aspect, the present invention is directed to novel immunological adjuvants for polysaccharide antigens, methods for the preparation of such adjuvants and the use thereof for rendering polysaccharide antigens more immunogenic.

DETAILED DESCRIPTION OF THE INVENTION

This invention as indicated above is directed to novel immunological adjuvants for polysaccharide antigens, methods of preparation and use. The immunological adjuvant which is useful for enhancing the immune response against polysaccharide antigens is comprised of:

(1) An emulsion system selected from the group consisting of:
  (A) a lipid emulsion system (LES) containing:
    (a) a metabolizable oil,
    (b) a low molecular weight polyol, and
    (c) lecithin, or
  (B) an oil-in-water emulsion system (O/W) containing:
    (a) a light hydrocarbon non-biodegradable oil or a biodegradable oil, and
    (b) a detergent,
(2) a refined detoxified endotoxin (RDE), and optionally,
(3) trehalose dimycolate, (TDM).

The present invention therefore provides a method whereby polysaccharide antigens may be rendered more immunogenic when combined with certain biological adjuvants in a biodegradable lipid emulsion system or in an oil-in-water emulsion system. The immune responses elicited by the polysaccharide antigens and the adjuvant systems of this invention differ markedly from the responses induced by the antigen alone in several respects. It has been observed that the adjuvantized antigen stimulates more antibody production, as measured by higher titers, than can be induced by the antigen alone. Additionally, the adjuvantized antigen mixture stimulates the production of IgG-class antibody with a higher titer than that obtained with the antigen alone. It has also been observed that the adjuvantized-antigen mixture of the present invention elicits immunological memory, as evidenced by a higher antibody response following a second injection of antigen than is obtained after primary immunization.

Prior to the present invention, no adjuvants of any type have ever been reported as being effective immunopotentiators of pure polysaccharide antigens. Hence, the present invention provides a means for enhancing the immunogenicity of polysaccharide antigens which heretofore had not existed. Accordingly, the adjuvants of the present invention are useful in stimulating both primary and secondary (i.e., memory) immune responses of warm blooded animals to vaccines containing polysaccharide antigens from a variety of sources. For example the polysaccharide antigens which can be employed with the adjuvants of the present invention include those purified from the capsules of bacteria such as *Streptococcus pneumoniae, Neisseria meningitidis, Klebsiella pneumoniae, Salmonella typhi,* or *Hemophilus influenzae*. Other polysaccharide antigens, such as can be obtained from capsules or cell walls of fungi or cell walls of gram-positive and gram-negative bacteria can also be employed with the adjuvants of the present invention. The only requirement of the polysaccharide antigen is that the immune response elicited by such antigen is one which can be enhanced by the presence of a suitable biological adjuvant.

As indicated previously, many polysaccharide antigens are known to stimulate the immune system. However the response elicited is primarily the IgM type of antibody without the ability to induce immunological memory for a secondary response. Thus, in the present invention an emulsion (with LES or O/W) is formed which contains the polysaccharide antigen and biological adjuvant. This results in presentation of the antigen in a particulate form to cells of the immune system, in slow antigen release to the immune system, and in a stimulation of progenitor cells involved in the immune response.

As indicated above, the immunological adjuvant of the present invention is comprised of two components. The first component is either a lipid emulsion system (LES) or an oil-in-water emulsion system (O/W). The second component is one or more refined detoxified endotoxin biological adjuvants. The lipid emulsion system (LES) contains a metabolizable oil, a low molecular weight polyol, and lecithin. In practice it has been found that the metabolizable oil used in the LES is preferably a fatty oil comprised mainly of diglycerides and triglycerides of oleic and linoleic acids. Particularly preferred are the fatty vegetable oils such as those contained in, or obtained from, peanut oil, sunflower seed oil, safflower seed oil, corn oil and the like. Other oils such as olive oil, cottonseed oil or squalene can also be employed in the adjuvants of the present invention. Thus, it is preferable that the oil be metabolizable, compatible with the components of the emulsion system and the bacterial adjuvant itself, and be effective in combination with the other components in enhancing the immune response against polysaccharide antigens.

In practice, a wide variety of polyols can be utilized in the lipid emulsion system. The polyols employed are low molecular weight polyols which are liquid, miscible with the metabolizable oil, and in which the lecithin component is soluble. Suitable polyols include, among others, ethylene glycol, 1,2-propane diol, 1,3-propane diol, glycerin, 1,4-butane diol, 1,3-butane diol, 1,2,4-butane triol, 1,5 pentane diol and the like.

As indicated, the third component of the lipid emulsion system is lecithin. The term "lecithin" as used throughout the specification and appended claims is intended to encompass any of a group of phospholipids having the general formula:

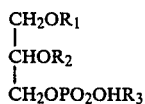

wherein $R_1$ and $R_2$ are fatty acids containing up to 22 carbon atoms and $R_3$ is choline. These phospholipids are usually a mixture of the diglycerides of stearic, palmitic, linoleic or linolenic fatty acids linked to the choline ester of phosphoric acid.

In practice, it has been found that the non-aqueous portion of the lipid emulsion system should preferably contain from about 30 to about 60 weight percent of the metabolizable oil, from about 30 to about 60 weight percent polyol and from about 1 to about 15 weight percent lecithin.

To illustrate, the preparation of the lipid emulsion system one part (10 grams) of sterile lecithin was dissolved in 10 parts (100 grams) of white glycerin by gentle heating at 60° C. on a hot plate while stirring with a magnetic bar. Prior to use, the glycerin was passed through a 0.2 micrometer filter unit to sterilize. Thereafter, the glycerin and lecithin mixture was placed in a sterile blender cup and 10 parts peanut oil (100 grams; sterilized by means of a 0.2 micrometer filter) was slowly added to the glycerin and lecithin mixture while blending at a moderate speed.

As previously indicated, the first component of the immunological adjuvant may be an oil-in-water (O/W) emulsion system instead of the lipid emulsion system. This O/W system can be comprised of a metabolizable oil such as squalene, or a non-metabolizable oil such as squalane, light mineral oil, 7-n-hexyloctadecane, Conoco superoil or Drakeol 6 VR mineral oil (produced by the Pennreco Company, Butler, Pa.). The oil-in-water emulsion also contains a detergent. The amount of detergent is typically between about 0.02 and 0.20, and preferably between about 0.10 and 0.20, percent by volume relative to the aqueous portion of the emulsion. Any common detergent material may be used, including Tween-80 and Arlacel (produced by the Atlas Chemical Company). The oil should comprise between about 0.5 to 3% of the total volume of the emulsion. The components employed in the lipid emulsion system and in the oil-in-water system are, of course, highly refined and of a pharmaceutically acceptable grade.

The second component of the immunological adjuvant is a refined detoxified bacterial adjuvant such as refined detoxified endotoxin. The detoxified endotoxin, hereinafter also referred to as RDE, is obtained from Re mutant strains of Salmonella. The detoxified endotoxin can also be obtained from other enterobacteriaciae as disclosed in U.S. Pat. No. 4,436,728 which is incorporated herein by reference. The detoxified endotoxin can also be prepared synthetically and by genetic engineering techniques. Another aspect of the second component is the optional addition of trehalose dimycolate (TDM). TDM may be obtained from any mycobacteria including, but not limited to M. avium, M. phlei, M. tuberculosis (strains H37RV and Ayoma B), M. bovis—BCG, M. smegmatis, M. kansaii, or M. bovinis; TDM may also be obtained from Nocardia rubra and Corynebacterium diphtheriae. TDM may be prepared as disclosed in U.S. Pat. No. 4,505,900 which issued Mar. 19, 1985.

Preparation of the polysaccharide vaccines incorporating LES is as follows: The second component(s) (RDE and, optionally, TDM) dissolved in chloroform:methanol 4:1 are placed in a sterile vial and the solvent is evaporated under a stream of sterile nitrogen. Polysaccharide antigen in sterile saline is added to the second component(s), followed by thorough mixing. In practice, to about three volumes of the polysaccharide antigen-bacterial adjuvant mixture is added one volume of the LES mixture prepared as described above, and this aqueous-oil mixture is blended in a vortex machine or in a blender until a white milky emulsion is obtained. Blending of the two components to obtain the emulsion is usually accomplished in from 2 to 5 minutes. The concentration of polysaccharide antigen in the final emulsion is from about 0.1 to 1000 micrograms per 0.2 milliliter; the concentration of RDE is from about 25 to about 200 micrograms per 0.2 milliliter; and the concentration of TDM, when present, is from about 50 to 400 micrograms per 0.2 milliliter.

Although the optimum ratio of the two phases of the LES-containing form of the immunological adjuvant is about three volumes of the polysaccharide antigen-detoxified bacterial adjuvant saline solution to about one volume of the lipid emulsion system, the ratio of the lipid emulsion system to the antigen-anjuvant solution can vary from about 1 to 1 to about 1 to 8, with about a 1 to 3 ratio being preferred.

An illustration of the oil-in-water system is as follows: 5 mg of RDE and 10 mg of TDM, each dissolved in chloroform:methanol 4:1, are introduced into a 350 ml tissue homogenizer (Bell-co). The solvent is evaporated from the RDE-TDM mixture with a stream of sterile nitrogen. This is followed by the addition of 2 ml of sterile oil (Drakeol 6 VR mineral oil [Pennreco Company, Butler, PA], light mineral oil, squalane, squalene, 7-n-hexyloctadecane) and the mixture is homogenized for 1 minute using a motor-driven pestle, until an oil-paste consistency is obtained. 98 ml of 0.2 percent Tween-80 in saline is then introduced into the homogenizer. Using a motor-driven pestle, the mixture is then further homogenized for about 4 to 5 minutes until an emulsion is obtained.

An appropriate amount of polysaccharide antigen in water is added to the liquid emulsion, which is then mixed by repeated aspirations and injections using a syringe and a 20 gauge needle for at least two minutes until the resulting emulsion gives a cloudy-milky appearance.

The oil-in-water emulsion may optionally be lyophilized by dispensing 5 ml into a 10 ml Wheaton serum vial. The vial is frozen in a Revco freezer at a temperature of −95° C. and lyophilized in a sterile container on a Labconoco freezer dryer. The vial is then capped using sterile technique. The lyophilized RDE-TDM emulsion is reconstituted by injection of 5 ml sterile water containing the desired concentration of polysaccharide antigen. It is emulsified by repeated aspirations and injections using the syringe for at least two minutes until the resulting emulsion gives a cloudy-milky appearance.

By either of the above processes, (i.e., LES or O/W) emulsions are obtained of the aqueous polysaccharide antigen solution which results in a slow release of the antigen, a prolongation of antigenic stimulation, and a cellular stimulation close to the antigen which is induced by the detoxified bacterial adjuvant(s). This combination of activities enhances the host's response to the antigen as is evident from the tables in the examples.

As noted above, the immunological adjuvant(s) may optionally contain trehalose dimycolate in addition to the refined detoxified endotoxin. Trehalose dimycolate (TDM), may be obtained as indicated in U.S. Pat. No. 4,505,900, from the organisms such as, for example, *M. avium, M. phlei, M. tuberculosis* (Strain H 37 RV and Ayoma B), *M. bovis* BCG, *M. smegmatis, M. kansasii, Nocardia rubra, M. bovinis* and *Corynebacterium diphtheriae*.

Bacteria such as *M. avium* are grown, harvested and then heat killed. The cell mass is then extracted with several solvents, leading to the isolation of an active, solvent soluble fraction. This fraction is further purified by a series of solvent extractions to provide crude TDM. (See Biologically Active Components from Mycobacterial Cell Walls. I. Isolation and Composition of Cell Wall Skeleton and Component P3; Azuma, et al., Journal of the National Cancer Institute, Volume 52, pgs. 95-101, 1974, incorporated herein by reference.) As disclosed in Azuma et al., crude TDM may then be further purified by centrifugal microparticulate silica gel chromatography to give purified TDM. Purification of TDM may also be accomplished by the procedure disclosed in copending application Ser. No. 372,843, filed Apr. 29, 1982, which is assigned to the same assignee as the present invention.

When employed in the adjuvant system, the trehalose dimycolate is used in a concentration of from about 50 to about 5000 micrograms per milliliter, and more preferably from about 250 to about 2000 micrograms per milliliter.

As indicated above, the immunological adjuvants of the present invention in admixture with a variety of polysaccharide antigens enhance the immune response against such antigens and hence are useful in a variety of vaccines for both veterinary and human hosts. In practice it has been found that the refined detoxified endotoxin is used in a concentration of from about 25 to about 200 micrograms per dose with a particularly enhanced immune response being elicited at approximately 100 micrograms per dose. The trehalose dimycolates are preferably used in a concentration of from about 50 to about 400 micrograms per dose. If desired, other components or additives can be employed in conjunction with the adjuvants of the present inventions.

In the examples below, the passive hemagglutinin assays using dextran and SSS III polysaccharides were conducted as follows:

Protocol for Passive Hemagglutinin (HA) Assay Using Dextran

Five ml of sheep red blood cells (SRBC) in Alsever's solution was washed 5 times in saline. Palmitoyl-dextran was dissolved in saline at a concentration of 1 mg/ml and 0.5 ml (500 µg palmitoyl-dextran) was added to 5 ml of 10% washed SRBC solution. This mixture was mixed well and incubated for 30 min at 37° C. The dextran-SRBC solution was washed 5 times in saline and then the cells were resuspended at 10% concentration.

Using a V-bottom 96-well microtiter plate, serum samples were diluted in 2-fold steps using a 0.5% bovine serum albumin (BSA) saline buffer. Final volume in each well was 50 µl. To each well was added 50 µl of 0.5% dextran-SRBC. Plates were incubated at room temperature overnight.

To an identical set of microtiter plates, 50 µl of 0.1M 2-mercaptoethanol was added following the dilution of the serum samples, and this was then followed by 50 µl of the dextran-coated SRBC.

Protocol for Passive Hemagglutination (HA) Assay Using SSS III Polysaccharide

Five ml of sheep red blood cells (SRBC) was washed 5 times in saline (0.85%). SSS III polysaccharide was dissolved in saline at 1 mg/ml. To 0.5 ml of packed SRBC were added: (1) 1 ml saline and (2) 1 ml of SSS III in saline (1000 µg). The mixture was gently vortexed and 1 ml of 0.1% chromic chloride ($CrCl_3.6H_2O$) in saline was added dropwise while vortexing. The mixture was allowed to stand at room temperature for 5 minutes. The SSS-III coated SRBC were washed 5 times in saline and resuspended as a 10% cell suspension in saline.

The serum from individual mice in each group was diluted in 2-fold steps in wells of a V-bottom 96-well microtiter plate. The starting dilution was 1:10 and the final volume of diluted serum per well was 50 µl.

To each well containing diluted serum was added 50 µl of SSS III-coated SRBC (0.5% cell suspension) and the plates were incubated at room temperature overnight. To an identical set of microtiter plates, 50 ul of 0.1M 2-mercaptoethanol was added after dilution of serum samples and this was then followed by 50 µl of the coated SRBC.

In the examples which follow, the dextran, palmitoyl-dextran and capsuler polysaccharide (SSS III) from the type III *Streptococcus pneumoniae* were provided by Dr. P. J. Baker of the N.I.H. Laboratory of Miciobial Immunity, Bethesda, Md.

The following examples are illustrative of the present invention:

EXAMPLE 1

In this experiment, BALB/C mice (6 mice/group) were given a subcutaneous injection (0.2 ml/animal) of the following: Group 1, 100 µg dextran in saline; Group 2, 100 µg dextran + 50 µg RDE in saline; Group 3, 100 µg dextran + 50 µg RDE in saline emulsified in an equal volume of LES lipid emulsion; Group 4, 100 µg dextran emulsified in a vial containing a lyophilized oil-in-water emulsion of 50 µg RDE + 50 µg TDM/dose; Group 5 received no antigen.

On day 20 after primary immunization, all mice in each group received a second injection that was prepared the same way as the first injection.

Individual serum samples were collected by serial bleedings at various times after immunization.

The results obtained are set forth below in Table I:

TABLE I

Passive hemagglutinin (HA) titers of serums from
mice immunized with the polysaccharide antigen Dextran
alone or in combination with RDE and other adjuvants
in various types of solutions

| Group | Treatment | Reciprocal of HA Titers (Days After Immunization) | | | |
|---|---|---|---|---|---|
| | | 6 | 16 | 30 | 48 |
| 1 | Dextran[a] | 163 (15)[b] | 340 (33) | 672 (54) | 240 (60) |
| 2 | Dextran + RDE | 800 (50) | 1228 (126) | 2368 (248) | 1386 (168) |
| 3 | Dextran + RDE + (LES) | 928 (76) | 2668 (660) | 3200 (400) | 2816 (232) |
| 4 | Dextran + RDE + TDM (Oil-in-water) | 373 (10) | 1120 (88) | 1813 (173) | 1493 (163) |
| 5 | None | 20 (10) | 40 (20) | 40 (20) | 10 (10) |

[a]All groups receiving antigen were injected subcutaneously on day 0 and on day 20.
[b]Results are expressed as the average reciprocal titer for each group. Starting dilution for each serum sample was 1:10. Numbers in parenthesis are the average titers of serums treated with 0.1 M 2-mercaptoethanol. These represent IgG responses.

EXAMPLE 2

In this experiment, BALB/C mice were injected subcutaneously (0.2 ml) with polysaccharide antigen (0.5 μg/mouse) alone or in combination with RDE adjuvant as follows: Group 1, SSS III was administered as an aqueous solution; Group 2, SSS III aqueous solution was emulsified in a vial containing an oil-in-water emulsion of RDE (50 μg/mouse) and TDM (50 μg/mouse); Group 3, SSS III aqueous solution was added to RDE (100 μg/mouse) in aqueous solution and the mixture was added to an equal volume of LES and emulsified. Group 4, aqueous SSS III was added to aqueous RDE (50 μg/mouse) and mixed with an equal volume of aluminum hydroxide gel (Alhydrogel); Group 5 was not immunized.

All groups contained 10 mice that were 6 to 8 weeks of age. Mice in each group were given a second subcutaneous injection on day 21 consisting of SSS III (0.5 μg/mouse) emulsified in RDE-TDM oil-in-water emulsion. Numbers in parentheses represent the mean titer of these same sera after treatment with 0.1M 2-mercaptoethanol.

The results obtained are set forth in Table II below:

TABLE II

Passive hemagglutinin (HA) titers of sera from mice
immunized with 0.5 ug pneumococcal polysaccharide antigen (SSS
III) alone or in combination with RDE and other adjuvants.

| Group | Treatment | Reciprocal of HA Titers (Days After Immunization) | | | |
|---|---|---|---|---|---|
| | | 7 | 14 | 28 | 42 |
| 1 | SSS III[a] | 240 (28)[b] | 56 (17) | 520 (164) | 182 (40) |
| 2 | SSS III + RDE + TDM (Oil-in-water) | 792 (104) | 240 (58) | 960 (400) | 1296 (480) |
| 3 | SSS III + RDE + LES | 1472 (232) | 448 (120) | 1152 (672) | 1536 (736) |
| 4 | SSS III + RDE + Alhydrogel | 80 (10) | 23 (12) | 100 (26) | 62 (8) |
| 5 | None | 10 (0) | 20 (15) | 20 (10) | 10 (0) |

[a]SSS III is the purified capsular polysaccharide from type III Streptococcus pneumoniae. The mice were immunized subcutaneously on day 0 and on day 21.
[b]Results are expressed as the average reciprocal titer for each group. Starting dilution for each serum sample was 1:10. Numbers in parenthesis are the average titers of serums treated with 0.1 M 2-mercaptoethanol.

EXAMPLE 3

In this experiment, BALB/C mice were given a subcutaneous injection (0.2 ml/mouse) of SSS III polysaccharide antigen alone or admixed with RDE in the LES lipid emulsion adjuvant system. All mice were given a second injection of SSS III (0.5 μg) admixed in the RDE-TDM oil-in-water emulsion 21 days after the primary immunization.

The results obtained are set forth below in Table III:

TABLE III

Passive hemagglutinin (HA) titers of sera from mice
immunized with various doses of pneumococcal
polysaccharide antigen (SSS III) admixed with RDE in the
lipid emulsion system (LES).

| Group | Treatment | Dose(ugs) | Reciprocal of HA Titers (Days After Immunization) | | | |
|---|---|---|---|---|---|---|
| | | | 7 | 14 | 28 | 42 |
| 1 | SSS III[a] | 0.5 | 240. (28)[b] | 56 (17) | 520 (164) | 182 (40) |
| 2 | SSS III + RDE | 0.5 + 100 | 1472 (232) | 448 (12) | 1152 (672) | 1536 (736) |
| 3 | SSS III + RDE | 0.5 + 50 | 3104 (240) | 624 (144) | 1152 (640) | 1280 (800) |
| 4 | SSS III + RDE | 0.25 + 100 | 512 (84) | 168 (50) | 1152 (386) | 800 (220) |

TABLE III-continued

Passive hemagglutinin (HA) titers of sera from mice immunized with various doses of pneumococcal polysaccharide antigen (SSS III) admixed with RDE in the lipid emulsion system (LES).

| Group | Treatment | Dose(ugs) | Reciprocal of HA Titers (Days After Immunization) | | | |
|---|---|---|---|---|---|---|
| | | | 7 | 14 | 28 | 42 |
| 5 | SSS III + RDE | 0.25 + 50 | 304 (48) | 144 (34) | 928 (320) | 928 (144) |

[a]SSS III is the purified capsular polysaccharide from type III *Streptococcus pneumoniae*. The mice were immunized subcutaneously on day 0 and on day 21.
[b]Results are expressed as the average HA titer of individual serum samples from serial bleedings. Numbers in parenthesis represent the average HA titers of serums treated with 0.1 M 2-mercaptoethanol. These represent IgG responses.

What is claimed is:

1. An immunological adjuvant useful for enhancing the immune response against polysaccharide antigens, comprised of:
    (1) an emulsion system selected from the group consisting of:
        (A) a lipid emulsion system (LES) containing:
            (a) a metabolizable oil,
            (b) a low molecular weight polyol, and
            (c) lecithin, or
        (B) an oil-in-water emulsion system O/W containing:
            (a) a light hydrocarbon non-biodegradable oil or a biodegradable oil, and
            (b) a detergent,
    (2) a refined detoxified endotoxin (RDE), and optionally,
    (3) trehalose dimycolate, (TDM).

2. The adjuvant of claim 1 wherein said adjuvant is utilized to enhance the immune response of warm blooded animals.

3. The adjuvant of claim 1 wherein said adjuvant is utilized to enhance the immune response of warm blooded animals against natural or synthetic polysaccharide antigens.

4. The adjuvant of claim 1 wherein said metabolizable oil is a fatty oil of vegetable origin comprised mainly of glycerides and triglycerides.

5. The adjuvant of claim 1 wherein said metabolizable or biodegradable oil is selected from the group consisting of peanut oil, sunflower seed oil, safflower seed oil, corn oil, olive oil, cottonseed oil or squalene.

6. The adjuvant of claim 1 wherein said non-biodegradable oil is selected from the group consisting of light mineral oil, squalane, 7-n-hexyl-octadecane, Drakeol 6 VR, or mineral oil.

7. The adjuvant of claim 1 wherein said lipid emulsion system is comprised of from about 30 to about 60 percent by weight of metabolizable oil; from about 30 to 60 percent by weight of a low molecular weight polyol, and from about 1 to 15 percent by weight of lecithin.

8. The adjuvant of claim 1 wherein said oil-in-water emulsion system is comprised of from about 0.5 to about 3 percent by weight of a light hydrocarbon non-biodegradable or a biodegradable oil and a detergent.

9. The adjuvant of claim 1 which contains a polysaccharide antigen.

10. The adjuvant of claim 9 wherein said antigen and said refined detoxified endotoxin are contained in a sterile saline solution.

11. The adjuvant of claim 10 wherein the concentration of antigen in said sterile saline solution is from about 0.1 to about 5000 $\mu$g/ml and the concentration of refined detoxified endotoxin in said sterile saline solution is from about 125 to 1000 $\mu$g/ml.

12. The adjuvant of claim 10 wherein said lipid emulsion system is comprised of from about 30 to about 60 percent by weight of metabolizable oil; from about 30 to 60 percent by weight of a low molecular weight polyol, and from about 1 to 15 percent by weight of lecithin, or the oil-in-water emulsion system comprised of from about 0.5 to 3 percent of a light hydrocarbon non-biodegradable oil or a biodegradable oil and a detergent, and the concentration of antigen in said sterile saline solution is from about 0.5 to about 5000 $\mu$g/ml and the concentration of refined detoxified endotoxin in said sterile saline solution is from about 125 to 1000 $\mu$g/ml.

13. A process of enhancing the immune response in warm blooded animals against a polysaccharide antigen, which comprises administering to said warm blooded animal an immune response enhancing amount of the immunological adjuvant of claim 9.

14. A process of enhancing the immune response in a host to a polysaccharide antigen, capable of eliciting said immune response, which comprises administering to said host an immune response enhancing amount of the immunological adjuvant of claim 12.

15. The process of claim 13 wherein the immunological adjuvant is administered by a single injection containing from about 25 to about 200 $\mu$g per dose of the refined detoxified endotoxin.

16. The process of claim 13 wherein the immunological adjuvant is administered by multiple injections, properly spaced, each containing about 25 to about 200 $\mu$g per dose of the refined detoxified endotoxin.

* * * * *